United States Patent [19]

Wallace et al.

[11] Patent Number: 5,426,039
[45] Date of Patent: Jun. 20, 1995

[54] DIRECT MOLECULAR CLONING OF PRIMER EXTENDED DNA CONTAINING AN ALKANE DIOL

[75] Inventors: Robert B. Wallace, Greenbrae; Franklin R. Witney, Novato, both of Calif.

[73] Assignee: Bio-Rad Laboratories, Inc., Hercules, Calif.

[21] Appl. No.: 118,387

[22] Filed: Sep. 8, 1993

[51] Int. Cl.[6] .......................... C12P 19/34; C12N 1/20
[52] U.S. Cl. .................................. 435/91.2; 435/91.4; 435/91.51; 435/252.33
[58] Field of Search .............. 435/6, 91.2, 91.4, 91.51, 435/252.33

[56] References Cited

U.S. PATENT DOCUMENTS

4,683,202  7/1987  Mullis ................................. 435/91.2
5,137,814  8/1992  Rashtchian et al. ............... 435/91.2

FOREIGN PATENT DOCUMENTS

0416817A2  3/1991  European Pat. Off. .
WO92/06189  4/1992  WIPO .

OTHER PUBLICATIONS

Gade, R., et al., "Incorporation of Nonbase Residues into Synthetic Oligonucleotides and Their Use in the PCR," GATA, 10(2): 61-65, (1993).
Takeshita, M., J. Biol. Chem. 262(21):10171-10179(1987).
GIBCO BRL Catalogue & Reference Guide 1992, copyright (1991) Life Technologies, Inc. p. 718.
Sambrook et al. Molecular Cloning: A laboratory manual (2nd Ed.) pp. 16.3-16.11 (1989).
Ugozzoli, L. et al., "Detection of Specific Alleles by Using Allele-Specific Primer Extension Followed by Capture on Solid Support," GATA, 9(4):107-112, (1992).
Newton, C. R., et al., "The Production of PCR Products with 5' Single-Stranded Tails Using Primers that Incorporate Novel Phosphoramidite Intermediates," Nucleic Acids Research, vol. 21, No. 5, pp. 1155-1162, (1993).
Schaaper, R. M., et al., "Depurination Causes Mutations in SOS-Induced Cells," Proc. Natl. Acad. Sci, USA, vol. 78, No. 3, pp. 1773-1777, (1981).
Seela, F., et al., "Oligodeoxyribonucleotides Containing 1,3-propanediol as Nucleoside Substitute," Nucleic Acids Research, vol. 15, No. 7, pp. 3113-3129, (1987).
Cuniasse, Ph., et al., "The Abasic Site as a Challenge to DNA Polymerase," J. Mol. Biol., 213, pp. 303-314, (1990).

Primary Examiner—Margaret Parr
Assistant Examiner—Lisa Arthur
Attorney, Agent, or Firm—Townsend and Townsend Khourie and Crew

[57] ABSTRACT

This invention relates to a method of cloning DNA produced by primer extension including PCR amplified, reverse transcriptase-generated or primer extended synthetic DNA. Specifically, it relates to a method in which alkane diol residue containing oligonucleotide primers are incorporated into DNA by primer extension followed by direct cloning of the target DNA. Following transformation, the host excises the alkane diol residue with its endogenous DNA repair machinery.

20 Claims, No Drawings

DIRECT MOLECULAR CLONING OF PRIMER EXTENDED DNA CONTAINING AN ALKANE DIOL

BACKGROUND OF THE INVENTION AND PRIOR ART

The ability to clone PCR products is of universal importance in the field of molecular biology. There are several general texts which address the subject, including Sambrook et. al., *Molecular Cloning—A Laboratory Manual* (2nd Ed.), Vol. 1–3, Cold Spring Harbor Laboratory, Cold Spring Harbor, N.Y., 1989 and *PCR Protocols A Guide to Methods and Applications* (Innis et. al. eds) Academic Press Inc. San Diego, Calif. (1990) which are incorporated herein by reference.

The *T. aquaticus* DNA polymerase 1 (Taq) has an activity which frustrated many people who attempted to clone PCR products before its nature was recognized. Taq has a weak terminal transferase activity under standard PCR conditions which typically causes the addition of a single adenosine (A) residue onto the 3' end of the amplified DNA product. Using traditional cloning strategies this residue must either be polished off using an exonuclease, or severed as a result of an internal restriction site cleavage by a restriction endonuclease prior to cloning. The problems with either of these strategies (detailed below) are familiar to those skilled in the art.

Polishing in preparation for blunt-ended cloning is generally straightforward, but blunt-ended cloning is often difficult, requiring relatively high concentrations of target and vector DNA. In addition, when a particular orientation of the cloned PCR DNA product relative to the vector is desired there must be an additional step of selecting for the desired orientation in the cloning protocol. Moreover, the cloning vector must either possess a blunt restriction site, or must itself be polished in order to ligate the PCR product into the vector. This requirement may necessitate additional cloning steps in order to create the desired final DNA construct.

Restriction enzyme digestion of PCR products for cloning typically requires that there be a known internal restriction site. This is usually accomplished by incorporating restriction sites into the PCR primers, a strategy with four distinct disadvantages. First, if the sequence of the PCR amplicon is unknown, then one may inadvertently select a restriction site in designing the primer which is also present in the target amplicon, leading to the cloning of unwanted DNA fragments. Second, restriction enzymes typically require a target with a minimum amount of surrounding DNA in order to recognize the restriction site in the proper context for cleavage to occur; thus, in designing a primer it is necessary to incorporate DNA residues between the restriction site and the end of the DNA molecule. The number of residues which are necessary for establishing the proper context is specific to each restriction enzyme and not always known; moreover, the addition of extra bases beyond the restriction site can be costly, particularly when it is done on a routine basis. Third, in some restriction enzymes the recognition site and the cleavage site are separated (e.g., HphI), which generally makes it impossible to use them in the cloning strategy. Finally, the addition of restriction sequences and the necessary contextual DNA for endonuclease cleavage reduces the specificity of the primer for the amplicon, a problem which is especially acute when attempting to use degenerate primers in the PCR amplification.

More recently, persons of skill have taken advantage of the terminal transferase activity of taq by designing cloning vectors to utilize the overhanging 3' A residue found on PCR DNA products (Hernstadt et. al., international patent application number PCT/US 91/07147, International Publication Number WO 92/06/06189 (4-16-92)). While this strategy is certainly useful, it is limited to a subset of all possible vectors, requiring many investigators to re-clone the cloned PCR product to create a desired construct.

The current methodology substantially overcomes each of the above enumerated problems. In general, an alkane diol residue such as 1,3-propanediol is incorporated into the PCR primer during oligonucleotide synthesis, which acts as a block to DNA chain elongation by taq during PCR. By strategically selecting the 5' ends of the PCR primers during oligonucleotide synthesis it is possible to generate a defined 5' overhang on all PCR products, without the need for further treatment. After ligating the PCR products into the vector of choice and transforming a bacterial cell such as *E. coli*, the non-basic residue is excised from the transformation vector by the cell's endogenous DNA repair machinery.

The generation of cDNA from mRNA is a commonly practiced technique in the field of molecular biology. It is often necessary to create a clone of a gene which lacks introns—particularly when the gene is to be expressed in a prokaryotic cell, which in general do not process their RNA to splice out introns. If a gene's product is of commercial interest it is often easiest given the current state of the art to express the gene in a bacterial cell culture and recover the protein in bulk.

cDNA libraries are often used in the process of isolating a gene of interest, or in order to help define the structure of a gene. cDNA libraries are superior to genomic libraries for a number of applications, including the creation of expression libraries and the creation of enriched libraries (libraries created from tissue in which the gene product is thought to be expressed). Due to the general utility of cDNA libraries, considerable effort and creativity has gone into methods which improve the heterogeneity of the library, which clone the cDNA constructs into expression vectors and which generate more nearly full-length clones.

All available methods for cDNA cloning suffer from common limitations. The creation of specific ends on the cDNA for cloning is problematic. Blunt ended cloning artificially enriches a library for the frequently found cDNAs in a sample due to the low rate of ligation, making it inappropriate for the generation of rare cDNAs. Adding adaptors to the cDNA molecule by incorporating restriction sites into the primers used in the first round of synthesis suffers from many of the same problems as the analogous strategy described above for PCR. Cloning the tailed cDNA molecule requires that the incorporated restriction site be cleaved by the appropriate restriction endonuclease, which may result in truncated cDNAs where there is an internal endonuclease site in the cDNA molecule. In addition, if the cleavage reaction is inefficient (i.e., if the endonuclease cleaves a site near the end of the molecule with lower than usual efficiency), artificial enrichment for frequently found cDNA molecules will occur.

The present invention overcomes the enumerated limitations of the prior art by incorporating an abasic residue into the first-round cDNA primer which blocks chain elongation by the DNA polymerase used in the cDNA synthesis at the site on the opposing strand opposite the abasic residue, creating a 5' overhang compatible with a cleaved vector. A strategy for generating a 5' overhang at the opposite end of the cDNA molecule using a primer complementary to a homopolymeric tail, in which the primer has an abasic residue is also described. Once the cDNA is ligated into the vector of choice, the construct is transformed into a bacterial cell via standard methods and the abasic residues are excised by the bacterial cell's endogenous repair machinery.

SUMMARY OF THE INVENTION

The present invention teaches a method for replicating the DNA of a DNA vector containing an alkane diol comprising transforming a bacterium with a replicable DNA vector having a 3' to 5' phosphate linkage interrupted with an alkane diol substituent of Formula I, and culturing the bacterium in a media in which the bacterium excises the alkane diol substituent and replicates the vector. An example of a bacterium which may be used in the present invention is *E. coli*. An example of an alkane diol of Formula 1 is 1,3 propane-diol. The replicated vector may be purified and transformed into a eukaryote if the original vector which was transformed into the bacterium is capable of replication in a eukaryotic cell.

This invention also includes a method wherein the replicable DNA vector used for transforming the bacterium comprises a first and a second part. The first part is obtained by amplifying a target nucleic acid sequence with a polymerase chain reaction primer consisting of a 3' segment with sequence complementary to the target nucleic acid and a 5' segment with sequence complementary to the second portion of the vector (described below) wherein the 3' and 5' segments of the primer are separated by an alkane diol substituent. The second part of the vector is obtained by cleaving a DNA construct with one or more restriction endonuclease to generate ends which are compatible for ligation with the ends on the first part of the vector. The first and second parts of the vector are ligated together to yield the DNA vector used to transform the bacterium described above. In general, the second part of the vector is usually dephosphorylated using a phosphatase such as calf intestinal alkaline phosphatase (CIAP) and the first part of the vector is phosphorylated using a kinase enzyme such as T4 polynucleotide kinase prior to ligation.

The primer and DNA construct may be selected so that they form a restriction endonuclease cleavage site upon ligation. The restriction endonuclease may be selected from any restriction endonuclease which generates 5' overhangs at the site of cleavage, including: AccI, Acc65, AhaII, AsuII, Asp718, AvaI, AvrII, BamH1, BclI, BglII, BsaNI, BspMII, BssHII, BspMI, BstEII, Bsu90I, DdeI, Eco0109, EcoR1, EcoRII, HindIII, HinPI, HinfI, HpaII, MaeI, MaeII, MaeIII, MboI, MluI, NarI, NcoI, NdeI, NdeII, NheI, NotI, PpuMI, RsrII, SalI, SauI, Sau3AI, Sau961, ScrFI, SpeI, StyI, TaqI, TthMI, XbaI, XhoI, XmaI and XmaIII. The restriction endonuclease cleavage site may be distinct from the restriction endonuclease recognition site for some enzymes such as HphI; nevertheless, as long as the sequence of the DNA construct comprising the second part of the vector is known, it is possible to utilize such restriction endonucleases in the cloning strategy.

The present invention additionally teaches a method wherein the target sequence encodes a protein which serves as a diagnostic marker for a genetic mutation, including but not limited to sickle cell anemia, alpha-1-antitrypsin deficiency, cystic fibrosis, and muscular dystrophy.

The present disclosure instructs one of skill in the construction of a cloning kit useful for cloning PCR-generated DNA fragments into a DNA construct. The kit comprises an alkane diol such as 1,3 propane diol in a form suitable for incorporation into oligonucleotides during synthesis on a standard DNA synthesizer and a DNA construct such as a pBR322, λ phage, or M13 phage derivative capable of reproduction upon introduction into a bacterial cell, said DNA construct containing one or more restriction endonuclease cleavage site. The kit would further comprise an instruction sheet explaining how to use the kit.

The present application also provides one of skill with a cDNA cloning method wherein the replicable DNA vector comprises a first and a second part. The first part is obtained by forming RNA-DNA heteroduplexes employing reverse transcriptase with mRNA as a template and using a primer with a 3' segment consisting of a sequence which is complementary to the 3' portion of the mRNA (e.g., the polyadenylated tail typically found on mRNA) and a 5' segment consisting of a sequence which is complementary to a sequence in the second part of the vector (described below) which is known to be cleaved by a restriction enzyme. The 3' and 5' segments are separated by an alkane diol substituent such as 1,3 propane diol. The restriction endonuclease cleavage site is selected from the cleavage sites of restriction endonucleases which generate a 5' overhang as described above. The RNA-DNA heteroduplex generated by the cDNA is partially digested with an RNA endonuclease such as RNase H to generate RNA primers. These primers are then used by subsequent rounds of primer extension using a template-dependant DNA polymerase. The second part of the vector is generated by cleaving a DNA construct with restriction endonucleases to generate a 5' overhang complementary to the 5' overhang on the first part of the vector and a blunt end on the end of the second part of the vector 3' to the 5' overhang, said blunt end being compatible for purposes of ligation with the blunt end created on the first part of the vector above. The first and second parts of the vector are ligated to yield the DNA vector. Prior to ligation the first part of the vector is generally phosphorylated using a kinase enzyme such a T4 polynucleotide kinase and the second part of the vector is generally dephosphorylated using a phosphatase enzyme such as CIAP.

As an alternative approach for the cloning of cDNA, an RNA-DNA hetroduplex is formed by reverse transcription of mRNA. A suitable primer for this reaction would be an oligonucleotide with a 3' segment complementary to a specific sequence within the target mRNA, such as the poly A region, and a 5' segment complementary to a restriction enzyme cohesive end produced by a restriction enzyme which produces 5' cohesive ends upon cleaving a recognition sequence. These two segments should be separated by an alkane diol substituent such as 1,3 propane diol. The DNA produced in the RT reaction can then be "tailed" by terminal deoxynucleotide transferase to place a homopolymer tail on the 3' end of the DNA; for example, a poly A tail could be added to the DNA using dATP.

The DNA could then be converted to double stranded DNA. A suitable primer for this reaction would be an oligonucleotide with a 3' segment complementary to the homopolymer tail of the DNA and a 5' segment complementary to a restriction enzyme cohesive end produced by a restriction enzyme which produces 5' cohesive ends upon cleaving a recognition sequence. These two segments should be separated by an alkane diol substituent such as 1,3 propane diol. In the case of a poly A tail on the DNA, the same primer used to produce the heteroduplex could be utilized. Finally, the double stranded DNA with restriction enzyme cohesive sites on both ends can then be cloned in a suitable cleaved vector.

Included in the present invention is a cDNA library generation kit comprising a DNA construct consisting of a DNA sequence capable of replication in a bacterial cell and a primer with a 3' segment which is complementary to the 3' portion on a mRNA molecule (e.g., a poly dT sequence complementary to the 3' poly dA cap generally found on mRNA molecules). The primer also contains a 5' segment consisting of a sequence that is compatible for ligation to a sequence which is created by cleaving the replicable DNA construct. The primer's 3' and 5' segments are separated by an alkane diol substituent such as 1,3 propane diol. The kit may also contain a bacterial cell culture (e.g., a cell culture derived from an *E. coli* cell) in which the DNA construct is capable of replicating.

The invention also discloses a cDNA library generation kit comprising the following elements: (a) a DNA construct consisting of a DNA sequence capable of replication in a bacterial cell; (b) a primer with a 3' segment consisting of a sequence which is complementary to the 3' portion on a mRNA molecule and a 5' segment consisting of a sequence that is compatible for ligation to a sequence which is created by cleaving the replicable DNA construct in part (a), which primer segments are separated by an alkane diol substituent; (c) a terminal deoxynucleotide transferase enzyme; (d) a deoxynucleotide triphosphate; (e) a primer with a 3' segment consisting of a sequence complementary to a homopolymeric sequence composed of the deoxynucleotide triphosphate in part (d) and a 5' segment consisting of a sequence that is compatible for ligation to a sequence that is created by cleaving the DNA construct in part (a), which primer segments are separated by an alkane diol substituent, and (f) a bacterial cell culture in which the vector in part (a) is capable of replicating.

DETAILED DESCRIPTION

The present invention teaches a method for cloning PCR-amplified DNA, primer extended DNA, or reverse transcription-generated cDNA. The method allows for PCR and RT cloning into any vector with a restriction endonuclease cleavage site which leaves a 5' overhang upon cleavage by the restriction endonuclease. When cloning cDNA, an additional endonuclease site is needed in the cloning vector, when the end distal to the incorporated modified synthetic primer in the cDNA molecule is left blunt. In contrast, the PCR product has a 5' overhang on both ends allowing for cohesive-end cloning of the PCR product into a cloning vector. The vector chosen for cloning the target sequence may be replicable in a bacterium or replicable in both a bacterium and a eukaryotic cell.

The vector containing the target DNA may be cloned into a bacterial cell, which will excise the alkane-diol substituted residue out of the incorporated primer. After bacterial excision of the modified base, the sequence at the site of repair may form a restriction endonuclease cleavage site. Thus, the present invention teaches one of skill a simple method for cloning a target sequence in either prokaryotes or eukaryotes.

The following discussion of general methods used in the present invention is intended for illustrative purposes. It is expected that one of skill will recognize many alternative methods to those discussed as being sufficient to practice the invention.

GENERAL METHODS

Much of the nomenclature and general laboratory procedures referred to in this application can be found in Sambrook et. al., Molecular Cloning—A Laboratory Manual (2nd Ed.), Vol. 1-3, Cold Spring Harbor Laboratory, Cold Spring Harbor, N.Y., 1989 or in Berger and Kimmel, *Guide to Molecular Cloning Techniques, Methods in Enzymology* 152 (Academic Press, Inc., San Diego, Calif. (1987)). The manuals are hereinafter referred to as "Sambrook" or "Berger" respectively.

CLONING

An variety of methods for cloning DNA sequences into prokaryotic cells are well known in the art. Organisms which are commonly utilized as hosts for the amplification of a vector include Escherichia, Bacillus and Streptomyces. The most common bacterial hosts are various commercially available strains of *E. coli*, due to the ease with which the organism may be cultured and the wealth of information which is available regarding the cell's life-cycle, genetics, viruses and developmental regulation. The vectors most commonly used in *E. coli* are those derived from the pBR322 plasmid and those derived from λ or M13 phage, although several vectors unrelated to any of these are also common. The Sambrook and Berger manuals contains methodology sufficient to direct persons of skill through most cloning exercises.

A number of vectors detailed in Sambrook and elsewhere may be initially cloned into *E. coli* and then subsequently transferred into a eukaryotic system without any necessity for re-cloning that part of the vector which is of interest to the person of skill. Vectors capable of replication in both prokaryotic and eukaryotic cells are generally termed "shuttle vectors" and must contain at a minimum a eukaryotic and a prokaryotic origin of replication. Several shuttle vectors are commercially available which contain poly-cloning sites, selectable markers for both bacterial and eukaryotic cells, promoters for both bacterial and eukaryotic expression of the gene(s) of interest, and integration sequences for insertion of the vector into the eukaryotic genome. A few examples of vectors which may be amplified in bacteria and used for transformation in eukaryotic cells include the family of P element vectors for *Drosophila melanogaster*, a number of SV40-derived vectors for the transformation of COS cells, adenovirus-derived vectors for transformation in cells containing the appropriate transcription factor for RNA polymerase III, a variety of BPV-derived vectors and the YIp5-derived vectors of *Saccharomyces cerevisiae* (see Sambrook chapter 16 and Berger chapter 53 for an overview of different vectors which may be transferred between *E. coli* and eukaryotes). General techniques for shuttling DNA between prokaryotes and eukaryotes are also described in Cashion et. al., U.S. Pat. No. 5,017,478 which is incorporated by reference.

PCR

The use of PCR (Mullis et. al., U.S. Pat. No. 4,683,202 (1987)) in the field of molecular biology is well known. PCR has been adapted for many diverse purposes, including cloning, sequencing, forensics, diagnostics and cladistic analysis. The technique is detailed in several general sources which provide adequate guidance to one of skill to perform the technique, including Sambrook and *PCR Protocols A Guide to Methods and Applications* (Innis et. al. eds) Academic Press Inc. San Diego, Calif. (1990) (hereinafter "Innis").

The following PCR protocol is provided as a starting point for a person of skill, who will readily recognize that it is usually necessary to optimize reaction conditions, and that optimization is especially important when the technique yields inadequate results, or when an essentially repetitive task utilizing the technique needs to be performed. In general, a 100 μl reaction contains the following: 1 to $1 \times 10^7$ target molecules (generally about $1 \times 10^5$ to $1 \times 10^6$ target molecules); 1 pmol-100 pmol of each primer (generally about 20 pmol), the primer having a $T_m$ of from about 30° C. to about 70° C. (preferably greater than about 50° C.) 20 mM Tris-HCl (pH approximately 8.3 at 20° C.); 0.2 mM-5 mM $MgCl_2$ (generally about 1.5 mM $MgCl_2$; occasionally it may be helpful to substitute some of the $MgCl_2$ with $MnCl_2$); 25 mM KCl; 0.05% Tween 20; 100 μg autoclaved gelatin or nuclease-free bovine serum albumin; 5-200 μM of each dNTP (generally about 50 μM of each dNTP), and from 0.25 to 5 units (generally about 2 units) of taq DNA polymerase. Many practitioners prefer to add an oil phase on top of the aqueous phase to prevent evaporation of the reaction mixture and to prevent the reaction components from being distributed unevenly in the reaction tube upon heating. The reaction mixture is cycled through 15-65 (usually 20-35) of the following temperature variations (generally using a commercially available thermal cycler, occasionally performed by hand with 3 temperature baths): "denaturation" at 92°-96° C. for 0.25-1 min. (on the first cycle it is often better to leave the reaction mixture at 96° C. for 1-5 minutes), "primer annealing" at a temperature about 5° C. to 10° C. lower than the calculated $T_m$ for 30 seconds, "primer extension" at 72° C. for 1-3 minutes depending on the length of the target sequence to be amplified. Cycling is generally concluded with a final 72° C. extension for about 5 minutes and the reaction is stopped by chilling the reactants to about 4° C. and/or by the addition of EDTA in an amount approximately 8-fold greater than the quantity of $MgCl_2$ plus $MnCl_2$ plus any other divalent cation in the mixture.

cDNA CLONING

Sambrook and Berger provide adequate guidance to one of skill to make and clone cDNA and to generate cDNA libraries. The present invention utilizes a specific primer to generate the first strand of cDNA using mRNA as a template and a template-dependant reverse transcriptase enzyme (RT) such as the avian myeloblastosis virus reverse transcriptase (AMV) or the mouse Maloney leukemia virus reverse transcriptase (MMLV), both of which are commercially available from a variety of sources. The primer includes a 3' segment complementary to the 3' portion of the mRNA molecule of choice—generally a series of about 8-20 T residues which are complementary to the 3' poly adenylated cap typically found on mRNA molecules—and a 5' segment which is complementary to a restriction endonuclease cleavage site in a vector into which a person of skill wishes to clone the cDNA molecule. The 3' and 5' segments of the primer are separated by an alkane diol residue incorporated into the nucleotide chain which is capable of blocking the progression of the template-dependant DNA polymerase used to synthesize the DNA strand complementary to the strand synthesized by the RT. The result of blocking the synthesis of the second DNA strand is a 5' overhang on one end of the cDNA molecule and a blunt end on the other. Synthesis of the second DNA strand is typically performed using an RNA endonuclease to generate RNA primers for DNA synthesis (usually RNase H) out of the RNA molecule which was used as the template for synthesis of the first DNA strand. The template dependant DNA polymerase used in the reaction is capable of displacing the nicked RNA ahead of the primer that it uses to initiate transcription.

Generation of the 5' overhang on the DNA construct into which the cDNA is to be cloned is performed using a restriction endonuclease capable of generating a 5' overhang. Generation of the distal blunt end (i.e., end most distant from the 5' overhang) is performed either by cleaving the DNA construct with an appropriate endonuclease which is capable of generating blunt ends, or by cleaving the DNA construct with a restriction endonuclease followed by a polishing procedure. When cleaving the DNA construct with an endonuclease followed by a polishing procedure to generate the blunt end it is necessary to generate the blunt end prior to the cleavage which generates the 5' overhang, since the polishing procedure is generally capable of polishing the 5' overhang off as well.

As an alternative approach for the cloning of cDNA, an RNA-DNA hetroduplex is formed by reverse transcription of mRNA. A suitable primer for this reaction would be an oligonucleotide with a 3' segment complementary to a specific sequence within the target mRNA, such as the poly A region, and a 5' segment complementary to a restriction enzyme cohesive end produced by a restriction enzyme which produces 5' cohesive ends upon cleaving a recognition sequence. These two segments should be separated by an alkane diol substituent such as 1,3 propane diol. The DNA produced in the RT reaction can then be "tailed" by terminal deoxynucleotide transferase to place a homopolymer tail on the 3' end of the DNA; for example, a poly A tail could be added to the DNA using dATP. The DNA could then be converted to double stranded DNA. A suitable primer for this reaction would be an oligonucleotide with a 3' segment complementary to the homopolymer tail of the DNA and a 5' segment complementary to a restriction enzyme cohesive end produced by a restriction enzyme which produces 5' cohesive ends upon cleaving a recognition sequence. These two segments should be separated by an alkane diol substituent such as 1,3 propane diol. In the case of a poly A tail on the DNA, the same primer used to produce the heteroduplex could be utilized. Finally, the double stranded DNA with restriction enzyme cohesive sites on both ends can then be cloned in a suitable cleaved vector.

The use of terminal deoxynucleotide transferase enzymes such as calf thymus terminal transferase is well known in the art. See Berger, or Sambrook for a description of their properties. Terminal transferase using dGTP in generating homopolymeric tails used in cDNA cloning is especially useful because the terminal transferase reaction self-terminates after adding approximately 20 residues. See Berger p. 339. In this case it is necessary to use a primer with a 3' segment comprised of oligo dC, for example 8-20 dC residues, and a 5' segment complementary to a restriction enzyme cohesive end produced by a restriction enzyme which produces a 5' cohesive end. These two segments should be separated by an alkane diol substitutent such as 1,3 propane diol.

OLIGONUCLEOTIDE SYNTHESIS

The present invention involves the introduction of a non-replicable element into the oligonucleotides used in PCR reactions. More particularly, this invention provides for the incorporation of a alkane diol nucleotide analogue into the oligonucleotide chain during synthesis of the primer. In selecting the appropriate nucleotide analogues for incorporation into PCR or cDNA primers it is helpful to consider first the structure of naturally occurring nucleotide chains and then the available information on alkane nucleotide analogues.

A nucleoside is a pentose glycoside in which the aglycone is a heterocyclic base; upon the addition of a phosphate group the compound becomes a nucleotide. The major biological nucleosides are β-glycoside derivatives of D-ribose or D-2-deoxyribose. Nucleotides are phosphate esters of nucleosides which are acidic due to the hydroxy groups on the phosphate. The polymerized nucleotides deoxyribonucleic acid and ribonucleic acid store the genetic information which controls all aspects of an organism's interaction with its environment. The nucleosides of DNA and RNA are connected together via phosphate units attached to the 3 position of one pentose and the 5 position of the next pentose; thus they are phosphate esters of a 1,3-diol.

Several non-naturally occurring residues have been incorporated into synthetic DNA, including models for the abasic site, a naturally occurring lesion in DNA. In the present invention, a denoted alkane diol is incorporated into an acyclic analogue of either a nucleoside or a nucleotide which lacks the nucleobase and substitutes an alkyl carbon chain for the pentose residue. Many of the alkane residues of the present invention are commercially available from the Aldrich Chemical Company, Inc. Milwakee, Wis. (1,3-propane diol; 2-methyl 1,3-propane diol, 1,4 butane diol, and 1,5 pentane diol). March (March, *Advanced Organic Chemistry Reactions, Mechanisms and Structure* 4th ed J. Wiley and Sons (New York, 1992)) contains information sufficient to direct one of skill through the synthesis of alkane diols, which may be synthesized from commercially available precursors by a number of well known techniques, including: hydrolysis of lactones followed by reduction with LiAlH$_4$, hydrolysis of cyclic anhydrides followed by reduction by LiAlH$_4$, the Prins reaction, the Tollens reaction followed by a crossed Cannizzaro reaction, and treatment of gem-dihalo compounds with methylene halides and lithium dicyclohexylamide.

The construction of non-basic alkane phosphoramidite residues that may be incorporated into oligonucleotides is known in the art (Seela and Kaiser, *Nuc. Acids Res.* 15 No. 7: 3113-3129 (1987)), and several phosphoramidites of the present invention are commercially available, including 3-(4',4'-dimthoxytrityloxy) propyl-1-[(2-cyanoethyl)-(N,N-diisopropyl)]-phosphoramidite from Glen Research (Sterling Va.). The following brief protocol for the construction of phosphoramidites is provided as a starting point for one of skill, who will recognize that many experimental parameters and reagents may be altered.

Selective protection of the two hydroxyl groups on the alkane diol is achieved by a residue that is compatible with commercially available nucleotide synthesis machines, such as the 4,4-dimethoxytrityl residue derived from 4,4-dimethoxytrityl chloride. This is accomplished by mixing the alkane diol in an approximately 5-fold molar excess with the 4,4-dimethoxytrityl chloride in a two-fold molar excess of Hünig's base, generally under nitrogen at room temperature, followed by the addition of aqueous NaHCo$_3$ and extraction with dichloromethane. The organic layers are washed with water, dried over sodium sulfate, filtered and evaporated. The residue is separated by chromatography and the products analyzed via NMR. The monotritylated product is selected for phosphitylation, typically using the procedure developed by McBride (McBride and Caruthers *Tetrahedron Lett.* 24:245-248 (1983)), using chlorodiisopropylaminoethoxy phosphane in dichloromethane in the presence of N-ethyldiisopropylamine.

Oligonucleotide synthesis from the phosphoramidite versions of the nucleotides that DNA and RNA are composed from may be carried out on commercially available solid phase oligonucleotide synthesis machines (Needham-VanDevanter, D. R., et al., Nucleic Acids Res., 12:6159-6168 (1984)) or chemically synthesized using the solid phase phosphoramidite triester method described by Beaucage et. al. (Beaucage et. al., *Tetrahedron Letts.* 22 No. 20:1859-1862 (1981). The construction of oligonucleotides containing non-basic alkane residues is known in the art (See Newton et. al., *Nuc. Acids Res.* 21, No. 5:1155-1162 (1993); Seela and Kaiser, *Nuc Acids Res.* 15, No. 7:3113-33129 (1987); Eritja et. al., *Nucleos. Nuleot.* 6:803-814 (1987); Ugozzoli et. al., GATA 9:107-112 (1992); since the alkane diols of the present invention are phosphoramidites with the same reactive groups as the phosphoramidites employed in oligonucleotide synthesis they are used in automated DNA synthesis protocols in essentially the same manner as phosphoramidite nucleotide precursors.

Oligonucleotide primers were not purified prior to use. Purification of primers can be performed using reverse phase or anion-exchange HPLC and may also be carried out by denaturing or native acrylamide gel electrophoresis.

DEFINITIONS

Amplification refers to the process of creating multiple copies of a DNA sequence, which may be achieved by either the PCR reaction, or standard cloning methodologies.

Bacterium in this application refers to a prokaryotic organism.

Compatible for ligation denotes a condition in which the ends on a DNA molecule or the ends on multiple DNA molecules have the necessary structural elements for ligation to occur. It does not expressly denote whether a 5' phosphate group is present on the ends to be ligated. The structural elements are generally either blunt ends for blunt ligation, or ends with enough complementarity for cohesive ligation.

Distal, when used to indicate an region of a nucleic acid indicates the region most distant from the end which is referred to. Thus the region distal to a 5' region of a nucleic acid refers to the 3' terminal region of the DNA.

Eukaryotic cells are cells which contain at least one nucleus in which the cell's DNA is organized, or which are the differentiated offspring of cells which contained at least one nucleus. Eukaryotes are distinguished from prokaryotes which are cellular organisms which carry their DNA in the cell's cytoplasm.

Homology is used in general conformity with its accepted meanings in the fields of molecular evolution and organic chemistry. In the field of organic chemistry, a homologous series generally refers to a succession of normal hydrocarbons which differ by the addition or subtraction of a methylene group. In the field of molecular evolution, two DNA or RNA or amino acid sequences are homologous when they share a common ancestor. In this application the term homology applies to man-made constructs as well as to structures arising during evolution; thus all plasmids which were created from a parent plasmid or its descendants are homologous. Homology is distinguished from the term "similarity" which denotes sequence similarity of two or more DNA, RNA or amino acid sequences without regard to their origin, and from the term "analogy" which denotes a similar function of two molecules or structures with unrelated ancestry.

Media refers to a general composition suitable for growing bacteria in or upon. The media should allow for the operation of the bacterium's general biosynthetic pathways, including its DNA repair and synthesis machinery. It is a non-critical feature of the invention.

Non-replicable refers to the inability of a template-dependant polymerase to use a portion of a target nucleic acid as a template and resulting in the non-replication of that portion of the target nucleic acid.

Oligonucleotide refers to a nucleic acid sequence composed of two or more nucleotides. An oligonucleotide can be derived from natural sources but is often synthesized chemically. It may be of any length. It may be used as a primer, a probe or a component of a ligation reaction.

Phosphorylation refers to the introduction of a phosphoryl group into a compound through the formation of an ester bond between the compound and phosphoric acid.

Primer refers to an oligonucleotide which is used to initiate a template dependant polymerase such as DNA polymerase 1 (Klenow fragment). The primer is complementary to a portion of a template nucleic acid.

Primer extension refers to the process of elongation of a primer using a nucleic acid template and a template dependant polymerase. Using appropriate buffers, pH, salts and nucleotide triphosphates, a template dependant polymerase such a DNA polymerase 1 (Klenow fragment) incorporates a nucleotide complementary to the template strand on the 3' end of a primer which is annealed to the template.

A Region of a polynucleotide refers to the general area surrounding a structural feature of the polynucleotide, such as the termini of the molecule, an incorporated abasic residue, or a specific sequence.

Replicable DNA vectors are DNA constructs with the information necessary to direct a host cell to replicate the DNA construct. The DNA construct may encode some of the proteins necessary for its replication, or it may rely entirely upon the host cell's endogenous replication machinery.

Restriction endonuclease cleavage site denotes the site at which a known endonuclease cleaves DNA under defined environmental conditions.

Restriction endonuclease recognition site denotes the DNA site which is recognized by the endonuclease which brings about the cleavage reaction. The recognition site is distinct from the cleavage site for some enzymes, such as HphI.

Reverse transcriptase refers to an enzyme capable of synthesizing a DNA sequence using an RNA sequence as a template.

A Segment of a polynucleotide is a specific region of the polynucleotide.

Sequence identity in this application denotes two nucleic acid sequences which are either the same, or which when one is the complement of the other will be sufficiently complementary for the two strands to bind with a high degree of specificity under physiological conditions.

Target nucleic acid or target sequence refers to a sequence of DNA or RNA which the practitioner wishes to amplify.

Template refers to a nucleic acid containing a region sufficiently complementary to a primer that the primer can anneal to the template and a polymerase can copy the template to produce a complementary nucleic acid.

Template dependant polymerase refers to an enzyme that extends a primer annealed to a template, copying the template and producing a complementary nucleic acid.

EXAMPLES

The following examples are by way of illustration and are not intended to limit the claims. Persons of skill will readily recognize that the protocols of the examples could be modified in numerous non-critical ways.

EXAMPLE 1

Synthesis of Propane Diol-Substituted Oligonucleotides

The compound 3-(4,4''-Dimethoxytrityloxy)propyl-1-[(2-cyanoethyl)-(N,N-diisopropyl)]-phophoramidite was purchased from Glen Research (Sterling, Va.) and dissolved in dry acetonitrile at a concentration of 0.1M. The bottle was then attached to the appropriate position on an Eppendorf automatic DNA synthesizer (Ecosyn D 300, Eppendorf North America, Madison, Wis.) for the addition of non-standard phosphoramidites (i.e., residues other than A, C, G or T). The position of the non-standard residue (depicted as a "X" in Table 1 and 2) in the desired oligonucleotide was then programmed into the machine and synthesis performed according to the manufacturer's instructions. Oligonucleotides were deprotected and purified by polyacrylamide gel electrophoresis.

EXAMPLE 2

Direct Molecular Cloning of PCR Amplified DNA Using Propane-diol-substituted Oligonucleotide Primers Synthesis of propane-diol substituted oligonucleotide primers Primers containing propane diol are described in Table I. The 3' segments of the primers are complementary to Exon 26 of the human Factor VIII gene (GenBank locus HUMFVIII, accession number K01740) and the 5' segments are complementary to a restriction enzyme cohesive end, either BamHI or EcoRI. They were synthesized according to method of example 1 but were not purified. Rather, they were used directly after deprotection and ethanol precipitation. The primers were phosphorylated prior to their use in PCR. Approximately 1 nmol of each primer was phosphorylated in a 20 μl reaction containing 1 mM ATP, 30 units of T4 polynucleotide kinase (US Biochemical, Cleveland, Ohio) for 60 min at 37° C. followed by heat inactivation of the enzyme at 65° C. for 10 min.

TABLE 1

Oligonucleotide Sequences of Primers Used in the PCR Amplification of Human Factor F VIII.

| Sequence ID. No. | Oligonucleotide Designation | Oligonucleotide Sequence |
| --- | --- | --- |
| MDO49 (Seq. I.D. #1) | F8P2gatcc | GATCCXTTACTGAAGAAACCAGCAGG |
| MDO50 (Seq. I.D. #2) | F8P2gatc | GATCXTTACTGAAGAAACCAGCAGG |
| MDO52 (Seq. I.D. #3) | F8P1aattc | AATTCXGAGGATGCAATTGTTGAAAG |
| MDO53 (Seq. I.D. #4) | F8P1aatt | AATTXGAGGATGCAATTTGTTGAAAG |

X represents a propane-diol substituted residue, as described in Formula I where R = H and n = 1.

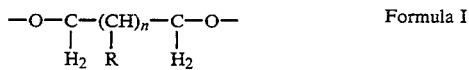

Formula I

Where n is equal to an integer from 1 to 3, and R represents H, $CH_3$, $CH_2CH_3$ or $(CH_2)_2CH_3$.

PCR

Primer pairs were used in PCR reactions, either pair MD053+MD050 or pair MD052+MD049. The template used was the DNA of a plasmid derived from "probe c" described by Antonarakis et al., *The New England Journal of Medicine* 313: 842–848 (1985). This plasmid contains nucleotide 7127 to nucleotide 9009 of HUMFVIII cloned at the EcoRI site of pTZ18ZU. The plasmid is approximately 4751 bp. (Mead et al., *Protein Engineering*, 1:67–74 (1986) available from BIO-RAD, Hercules, Calif.)

All PCR reactions were performed using 20 cycles of thermal cycling with the following conditions: 94° C., 1 min; 55° C., 30 sec; 72° C. for 1 min. The DNA polymerase used was Native-Taq DNA polymerase (Perkin-Elmer). The buffer used was that recommended by the supplier of the DNA polymerase. The template was EcoRI cleaved plasmid DNA.

Configuration of the Cohesive Ends

In the first experiment, two possible cohesive end configurations were tested:

Configuration 1: AATTXGAGG ...
+GATCXTTAC ...

Configuration 2: AATTCXGAGG ...
+GATCCXTTAC ...

The difference between the two configurations is that configuration 1 does not provide the "C" of the GAATTC EcoRI recognition site or the "C" of the GGATCC BamHI recognition site. Also, the length of the 5' cohesive end differs in the two configurations. There are 4 nucleotides before the propane diol in configuration 1, and 5 nucleotides before the propane diol in configuration 2.

Cloning of Human Factor VIII Amplicon

Separate PCR reactions for each pair of primers was performed. Each reaction contained 25 ng of template and 200 pmol of a primer pair. The products of the amplification reaction were monitored by agarose gel electrophoresis. An approximately 1 kb amplicon was seen for each primer pair. The remainder of the PCR reaction was purified using Prep-a-Gene (Bio-Rad Laboratories) according to the manufacturer's recommendations.

The vector pTZ18U (1.5 μg) was digested with EcoRI and BamHI in a 40 μl reaction for 2 hr at 37° C. The doubly digested vector was purified using Prep-a-Gene (Bio-Rad Laboratories) according to the manufacturer's recommendations. The doubly digested DNA was then dephosphorylated in a 49 μl reaction using 26 units of calf intestinal alkaline phosphatase (US Biochemical, Cleveland, Ohio) at 37° C. for 15 min followed by an additional 26 units of calf intestinal alkaline phosphatase at 55° C. for 45 min. The reaction was stopped by adding 40 μl of $H_2O$, 10 μl of 100 mM Tris-HCl, 1M NaCl, 10 mM EDTA, 0.5% SDS pH 8.0 and 5 μl of 10% SDS followed by heating to 68° C. for 15 min. The dephosphorylated vector was then purified with Prep-A-Gene kit.

The amplicons from the PCRs were ligated with the vector in a 20 μl reaction which contained approximately 50 ng of dephosphorylated vector, approximately 600 ng of PCR product (from either the configuration 1 primer pair or the configuration 2 primer pair), 1 mM ATP, 3 units to T4 DNA ligase (Bio-Rad) in appropriate buffer. Ligations were performed at 16° C. overnight. The ligation reactions were then used to transform JS5 (Bio-Rad) by electroporation and plated on X-gal containing LB/Amp plates.

Both primer pairs produced white colonies. White colonies were chosen at random, mini-plasmid preparations prepared and the plasmid DNAs analyzed by restriction enzyme digestion and gel electrophoresis as well as by DNA sequencing. The results of the analysis showed that 5 of 10 colonies from configuration 2 primer pair amplicon and 9 of 10 using configuration 1 primer pair amplicon contained the correct insert.

DNA sequencing of one of the plasmids from a configuration 2 primer pair showed, surprisingly, that the position occupied by the propane diol was deleted in the resulting cloned DNA.

EXAMPLE 3

Direct Cloning Using Primer Pairs Designated Configuration 3

The propane diol residue was deleted in the process of cloning using different configurations for the cohesive ends of the PCR primers, Configurations 1 and 2 are described above, In configuration 3, the "C" of the GAATTC EcoRI recognition site and the "T" of the AAGCTT HindIII recognition site is positioned after the propane diol residue, Thus the recognition sequence is made up of 4 nucleotides before the propane diol and one after the propane diol, Configuration 3: AATTXCTTA ...
+AGCTXTCTT ...

TABLE 2

Oligonucleotide Sequences of Primers Used in the PCR Amplification of Human Factor F VIII; Configuration 3.

| Sequence ID. No. | Designation | Sequence |
| --- | --- | --- |
| MD055 (Seq. I.D. #5) | F8P3agctxt | AGCTXTCTTGAAATTTGTGATGGCCA |
| MD056 (Seq. I.D. #6) | F8P2aattxc | AATTXCTTACTGAAGAAACCAGCAGG |

X represents a propane-diol substituted residue, as described in Formula I.

The oligonucleotides were synthesized, deprotected and phosphorylated as described above, PCR amplifications were performed with 10 ng of template and 5 pmol of the configuration 3 primer pair, The amplicons were ligated to dephosphorylated EcoRI+HindIII doubly digested pTZ18U in a 10 µl reaction containing 25 ng of vector 2 µl amplicon generated with the configuration 3 primer pair, 1 mM ATP and 3 units of T4 DNA ligase (Bio-Rad) for 2,5 hr at 20° C. followed by heat inactivation of the enzyme at 65° C. for 10 min, The ligated material was used to transform JS5 by electroporation and plated on X-gal Amp/LB plates, Six white colonies were randomly picked and mini-plasmid DNA preparations made, The resulting plasmids were analyzed by restriction enzyme digestion and agarose gel electrophoresis, All 6 plasmids contained the correct insert. Three of them could be digested with EcoRI and HindIII. It was determined that the 3 that would not digest with both enzymes lacked the EcoRI site, but all 6 contained the expected HindIII site.

EXAMPLE 4

Direct Cloning of Primer Extended Synthetic DNA

This example describes the use of propane diol-substituted primers for the direct cloning of a DNA fragment. Two propane diol-substituted primers were synthesized with a region of complementarity as described in Table 1. A DNA polymerase was used to extend the hybridized primers up to the propane-diol substitution on the complementary strand. The resulting primer extension products were ligated into a cloning vector possessing a disruption in the reading frame of the beta-galactosidase alpha-chain gene and introduced into a lac− bacterium. Upon cloning of the primer extension products into the vector, the reading frame was restored and the bacterium displayed a lac+ phenotype. The presence or absence of a functional lac gene in a bacterium may be assayed by color selection on media containing X-gal. Bacterial colonies which are lac+ display a blue phenotype when grown on a nutrient plate containing X-gal. Lac− bacteria display a white phenotype.

Preparation of Lac− Derivative of Plasmid pTZ18

Plasmid pTZ18 (1 µg) was cleaved with BamH$_1$ in a reaction that contained 20 units of BamH$_1$ (Life Technologies, Gaithersburg, Md.) in 20 µl of the buffer recommended by the supplier of the enzyme for 1.5 hr at 37° C. followed by heat inactivation at 65° C. for 15 min. The cohesive ends were then filled in with T4 DNA polymerase (0.5 units) in a 30 µl reaction containing 3.3 µM dNTPs at 11° C. for 20 min followed by heat inactivation of the enzyme at 75° C. for 10 min. 0.15 µg of the resulting blunt-ended DNA was circularized using T4 DNA ligase (3 unit) in a 20 µl reaction containing 50 µM ATP and 15% polyethylene glycol at 20° C. for 1.5 hr followed by heat inactivation of the enzyme at 65° C. for 15 min. The ligated sample was diluted 1:3 and 0.5 µl used to transform JS5 host cells by electroporation and plated on X-gal containing Amp/LB plates. A white colony was selected. Mini-plasmid preparation of the DNA from the white colony showed that the plasmid retained the EcoR1 and HindIII sites but lost the BamH$_1$ site. The plasmid was designated pTZ18/+.

Preparation of Doubly Digest and Dephosphorylated pTZ18/+ pTZ18/+ (0.4 µg) was cleaved with HindIII (10 units, Life Technologies, Gaithersburg, Md.) and EcoRI (10 units, New England Biolabs) in a 20 µl reaction at 37° C. for 1.5 hr followed by heat inactivation of the enzymes at 65° C. for 10 min. 0.3 µg of the cleaved vector was dephosphorylated in a 30 µl reaction containing shrimp alkaline phosphatase (US Biochemical, Cleveland, Ohio) at 37° C. for 1 hr followed by heat inactivation of the enzyme at 65° C. for 15 min.

Direct Cloning of Primer Extended Synthetic DNA

Two oligonucleotides MD081 (Seq. I.D. #7), 5'AATTXCGAGCTCGGTACCCGGGGATCCT-CTAGAGT and MD080 (Seq. I.D. #8) control 5'AGCTXTGCATGCCTGCAGGTCGACT-CTAGAGGATC (X indicates propane diol residue as described in Formula 1) were synthesized. Approximately 1.2 nmol of each primer was mixed and phosphorylated in a 20 µl reaction containing 0.5 mM ATP and 30 units of T4 kinase (US Biochemical, Cleveland, Ohio) at 37° C. for 60 min followed by heat inactivation of the enzyme at 65° C. for 15 min. Two 4 µl aliquots of the phosphorylated oligonucleotide mixture were primer extended in 10 µl reactions containing 100 µM dNTPs with either T4 DNA polymerase (Bio-Rad Laboratories) at 11° C. for 20 min or Bst DNA polymerase (Bio-Rad Laboratories) at 65° C. for 3 min. Each reaction was stopped by heating; at 75° C. for 10 min in the case of T4 DNA polymerase and at 95° C. for 5 min in the case of Bst DNA polymerase. 12 pmol of the primer extended duplexes were ligated to the doubly-digested and dephosphorylated pTZ18/+ in 10 µl reactions, each containing 10 ng of vector, 1 mM ATP and 30 units of T4 ligase at 20° C. for 1.5 hr followed by heat inactivation at 65° C. for 15 min.

Each reaction was diluted 1:4 and 1 µl used to transform JS5 by electroporation. A mixture of blue and white colonies resulted. The blue colonies resulted from the cloning of the primer extended synthetic DNA.

FIG. 1:
Flow chart for Example 4

Primer extension:

MD81 5' pAATTXCGAGCTCGGTACCCGGGGATCCTCTAGAGT ——→DNA poly
MD80                                CTAGGAGATCTCAGCTGGACGTCCGTACGTXTCGAp5'
dNTPs 5' pAATTXCGAGCTCGGTACCCGGGGATCCTCTAGAGTCGACCTGCAGGCATGCA  (primer extension
       GCTCGAGCCATGGGCCCCTAGGAGATCTCAGCTGGACGTCCGTACGTXTCGAp5'  products)

Vector preparation and cloning:

pTZ18 ——→BamHI ——→ ___G      pGATCC___ ——→T49 poly ——→
                   ___CCTAGp         G___              dNTPs ___GGATC     pGATCC___  ——→blunt-end ligation ——→
___CCTAGp    CTAGG___          T4 ligase ___GGATCGATCC___ ——→transformation ——→white (PTZ18/+) ——→
___CCTAGCTAGG___

HindIII/EcoRI ——→double digested pTZ18/+ ——→shrimp alkaline phosphatase

——→doubly digested, dephosphorylated pTZ18/+ ——→+ primer extension products
                                                                T4 ligase ——→pTZ18 ——→transformation ——→blue

---

What is claimed is:

1. A method for replicating a DNA of a DNA vector containing an alkane diol comprising:
   (a) transforming a bacterium with a replicable DNA vector having a 3' to 5' phosphate linkage interrupted with an alkane diol bridge of Formula I, wherein said formula is represented as:

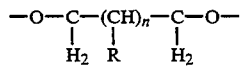

where n is an integer from 1 to 3 and R is either H, CH$_3$, CH$_2$CH$_3$, or CH$_2$CH$_2$CH$_3$; and,
   (b) culturing said bacterium in a medium permitting the bacterium to excise the alkane diol bridge and replicate the vector.

2. A method of claim 1 further comprising the steps of:
   (c) purifying the replicated vector DNA, and,
   (d) transforming a eukaryotic cell with the purified replicated vector DNA.

3. A method of claim 1 wherein the bacterium is an *Escherichia coli* and the alkane diol is 1,3 propane diol.

4. A method of claim 1 wherein the replicable DNA vector comprises a first and a second part and the vector is obtained by conducting before step (a) the steps of:
   (i) amplifying a target nucleic acid sequence with a polymerase chain reaction primer consisting of a 3' segment with sequence complementary to the target nucleic acid and a 5' segment with sequence complementary to the second part of the vector wherein the 3' and 5' segments of the primer are separated by an alkane diol bridge, said amplification reaction yielding the first part of the vector;
   (ii) cleaving a DNA construct with one or more restriction endonuclease to create the second part of the vector with ends which are compatible for ligation with the ends on the first part of the vector generated in step (i); and,
   (iii) ligating the first and second parts to yield the replicable DNA vector.

5. A method of claim 4 wherein the 5' segment of the primer will form a restriction enzyme cleavage site when ligated to the first part of the vector.

6. A method of claim 5 wherein the restriction enzyme cleavage site is selected from the group consisting of AccI, Acc65, AhaII, AsuII, Asp718, AvaI, AvrII, BamH1, BclI, BglII, BsaNI, BspMII, BssHII, BspMI, BstEII, Bsu90I, DdeI, EcoO109, EcoR1, EcoRII, HindIII, HinPI, HinfI, HpaII, MaeI, MaeII, MaeIII, MboI, MluI, NarI, NcoI, NdeI, NdeII NheI, Not1, PpuMI, RsrII, Sal1, SauI, Sau3AI, Sau961, ScrFI, SpeI, StyI, TaqI, TthMI, XbaI, XhoII, XmaI and XmaIII.

7. A method of claim 4 wherein said one or more restriction endonuclease comprises at least one restriction endonuclease selected from the group consisting of HphI and MboII.

8. A method of claim 4 wherein the target sequence encodes a protein which serves as a diagnostic marker for a genetic mutation.

9. A method of claim 8 wherein the genetic mutation causes sickle cell anemia, alpha-1-antitrypsin deficiency, cystic fibrosis, or muscular dystrophy.

10. A method of claim 1 wherein the replicable DNA vector comprises a first and a second part and is obtained by the conducting before step (a) the steps of:
    (i) forming RNA-DNA heteroduplexes employing reverse transcriptase with mRNA as a template and using a primer with a 3' segment consisting of a sequence which is complementary to the 3' portion of the mRNA and a 5' segment consisting of a sequence which is complementary to a sequence in the second part of the vector which is known to be cleaved by a restriction enzyme, and wherein the 3' and 5' segments of the primer are separated by an alkane diol bridge;
    (ii) treating the RNA-DNA heteroduplexes of step (i) with an RNA endonuclease to generate RNA primers for subsequent rounds of primer extension using a template-dependant DNA polymerase;

(iii) generating the first part of the vector with a template dependant DNA polymerase using the RNA primers of step (ii);

(iv) generating the second part of the vector by cleaving a DNA construct with restriction endonucleases to generate a 5' overhang complementary to the 5' overhang on the first part of the vector generated in step (iii), and a blunt end on the end of the second part of the vector 3' to the 5' overhang, said blunt end being compatible for purposes of ligation with the blunt end created on the first part of the vector in step (iii), and (v) ligating the first and second parts to yield the replicable DNA vector.

11. A method of claim 10 further comprising prior to step (v) the steps of:
(A) dephosphorylating the second part of the vector with a phosphatase enzyme, and
(B) phosphorylating the first part of the vector with a kinase enzyme.

12. A method of claim 10 wherein the sequence complementary to the 3' portion of the mRNA of step (i) comprises 8 or more sequential thymidine residues.

13. A method of claim 10 wherein the RNA endonuclease is RNAase H.

14. A method of claim 10 wherein the alkane diol is 1,3 propane diol, and wherein the second part of the vector is homologous to either pBR322 or phage λ.

15. A method of claim 10 wherein the restriction endonuclease is selected from the group consisting of AccI, Acc65, AhaII, AsuII, Asp718, AvaI, AvrII, BamH1, BclI, BglII, BsaNI, BspMII, BssHII, BspMI, BstEII, Bsu90I, DdeI, EcoO109, EcoR1, EcoRII, HindIII, HinPI, HinfI, HpaII, MaeI, MaeII, MaeIII, MboI, MluI, NarI, NcoI, NdeI, NdeII NheI, NotI, PpuMI, RsrII, Sal1, SauI, Sau3AI, Sau961, ScrFI, SpeI, StyI, TaqI, TthMI, XbaI, XhoII, XmaI and XmaIII .

16. A method of claim 1 wherein the replicable DNA vector comprises a first and a second part and is obtained by the conducting before step (a) the steps of:
(i) forming RNA-DNA heteroduplexes employing reverse transcriptase with mRNA as a template and using a primer with a 3' segment consisting of a sequence which is complementary to the 3' portion of the mRNA and a 5' segment consisting of a sequence which is complementary to a sequence in the second part of the vector which is known to be cleaved by a restriction enzyme, and wherein the 3' and 5' segments of the primer are separated by an alkane diol bridge;
(ii) adding homopolymeric tails onto the DNA synthesized in step (i) with a terminal deoxynucleotide transferase;
(iii) hybridizing a synthetic primer with a 3' segment complementary to the homopolymeric tails synthesized in step (ii) and a 5' segment complementary to the sequence in the second part of the vector which is known to be cleaved by a restriction enable, wherein the two segments are separated by an alkane diol bridge;
(iv) generating the first part of the vector with a template dependant DNA polymerase using the primers of step (iii);
(v) generating the second part of the vector by cleaving a DNA construct with restriction endonucleases to create ends compatible for ligation with the first part of the vector generated in (iv), and
(j) ligating the first and second parts to yield the replicable DNA vector.

17. A method of claim 16 wherein the sequence of the segment of the primer in part (i) which is complementary to the 3' portion of the mRNA comprises 8 or more sequential thymidine residues.

18. A cDNA library generation kit comprising:
(a) A DNA construct consisting of a DNA sequence capable of replication in a bacterial cell;
(b) A primer with a 3' segment consisting of a sequence which is complementary to the 3' portion on a mRNA molecule and a 5' segment consisting of a sequence that is compatible for ligation to a sequence which is created by cleaving the DNA construct in part (a), in which the 3' and 5' segments are separated by an alkane diol bridge, and
(c) A bacterial cell culture in which the vector in part (a) is capable of replicating.

19. A kit of claim 21 in which the bacterial cell line is derived from an *Escherichia Coli* bacterial cell, the DNA construct is homologous to pBR322 or phage λ and the primer has 8 or more consecutive thymidine residues.

20. A cDNA library generation kit comprising:
(a) a DNA construct consisting of a DNA sequence capable of replication in a bacterial cell;
(b) a primer with a 3' segment consisting of a sequence which is complementary to the 3' portion on a mRNA molecule and a 5' segment consisting of a sequence that is compatible for ligation to a sequence which is created by cleaving the DNA construct in part (a), which primer segments are separated by an alkane diol bridge;
(c) a terminal deoxynucleotide transferase enzyme;
(d) a deoxynucleotide triphosphate;
(e) a primer with a 3' segment consisting of a sequence complementary to a homopolymeric sequence composed of the deoxynucleotide triphosphate in part (d) and a 5' segment consisting of a sequence that is compatible for ligation to a sequence that is created by cleaving the DNA construct in part (a), which primer segments are separated by an alkane diol bridge, and
(f) A bacterial cell culture in which the vector in part (a) is capable of replicating.

* * * * *

UNITED STATES PATENT AND TRADEMARK OFFICE
CERTIFICATE OF CORRECTION

PATENT NO. : 5,426,039
DATED : June 20, 1995
INVENTOR(S) : Robert B. Wallace, et al.

It is certified that error appears in the above-indentified patent and that said Letters Patent is hereby corrected as shown below:

Column 26, claim 16, line 1, replace [enable] with --enzyme--.

Column 26, claim 19, line 29, replace [21] with --18--.

Signed and Sealed this

Twenty-seventh Day of February, 1996

*Attest:*

BRUCE LEHMAN

*Attesting Officer*  *Commissioner of Patents and Trademarks*

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i x ) FEATURE:
        ( A ) NAME/KEY: modified_base
        ( B ) LOCATION: 6
        ( D ) OTHER INFORMATION: /note="N represents a propane-diol
            substituted residue, as described in Formula I of
            the patent application."

( i x ) FEATURE:
        ( A ) NAME/KEY: misc_feature
        ( B ) LOCATION: 1..26
        ( D ) OTHER INFORMATION: /standard_name="PCR PRIMER MD049"

( x i ) SEQUENCE DESCRIPTION: SEQ ID NO:1:

GATCCNTTAC TGAAGAAACC AGCAGG                         2 6

( 2 ) INFORMATION FOR SEQ ID NO:2:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear (i i) MOLECULE TYPE: DNA (genomic)

(i i i) HYPOTHETICAL: NO (i x) FEATURE:
    (A) NAME/KEY: modified_base
    (B) LOCATION: 5
    (D) OTHER INFORMATION: /note="N represents a propane-diol substituted residue, as described in Formula I of the patent application."

(i x) FEATURE:
    (A) NAME/KEY: misc_feature
    (B) LOCATION: 1..25
    (D) OTHER INFORMATION: /standard_name="PCR PRIMER MD050"

(x i) SEQUENCE DESCRIPTION: SEQ ID NO:2:

GATCNTTACT GAAGAAACCA GCAGG      25

(2) INFORMATION FOR SEQ ID NO:3:

(i) SEQUENCE CHARACTERISTICS:
    (A) LENGTH: 26 base pairs
    (B) TYPE: nucleic acid
    (C) STRANDEDNESS: single
    (D) TOPOLOGY: linear (i i) MOLECULE TYPE: DNA (genomic)

(i i i) HYPOTHETICAL: NO (i x) FEATURE:
    (A) NAME/KEY: modified_base
    (B) LOCATION: 6
    (D) OTHER INFORMATION: /note="N represents a propane-diol substituted residue, as described in Formula I of the patent application."

(i x) FEATURE:
    (A) NAME/KEY: misc_feature
    (B) LOCATION: 1..26
    (D) OTHER INFORMATION: /standard_name="PCR PRIMER MD052"

(x i) SEQUENCE DESCRIPTION: SEQ ID NO:3:

AATTCNGAGG ATGCAATTGT TGAAAG      26

(2) INFORMATION FOR SEQ ID NO:4:

(i) SEQUENCE CHARACTERISTICS:
    (A) LENGTH: 26 base pairs
    (B) TYPE: nucleic acid
    (C) STRANDEDNESS: single
    (D) TOPOLOGY: linear (i i) MOLECULE TYPE: DNA (genomic)

(i i i) HYPOTHETICAL: NO (i x) FEATURE:
    (A) NAME/KEY: modified_base
    (B) LOCATION: 5
    (D) OTHER INFORMATION: /note="N represents a propane-diol substituted residue, as described in Formula I of the patent application."

(i x) FEATURE:
    (A) NAME/KEY: misc_feature
    (B) LOCATION: 1..26
    (D) OTHER INFORMATION: /standard_name="PCR PRIMER MD053"

(x i) SEQUENCE DESCRIPTION: SEQ ID NO:4:

AATTNGAGGA TGCAATTTGT TGAAAG      26

(2) INFORMATION FOR SEQ ID NO:5:

(i) SEQUENCE CHARACTERISTICS:

(A) LENGTH: 26 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (ix) FEATURE:
         (A) NAME/KEY: modified_base
         (B) LOCATION: 5
         (D) OTHER INFORMATION: /note="N represents a propane-diol
               substituted residue, as described in Formula I of
               the patent application."

(ix) FEATURE:
         (A) NAME/KEY: misc_feature
         (B) LOCATION: 1..26
         (D) OTHER INFORMATION: /standard_name="PCR PRIMER MD055"

(xi) SEQUENCE DESCRIPTION: SEQ ID NO:5:

AGCTNTCTTG AAATTTGTGA TGGCCA                                                              26

(2) INFORMATION FOR SEQ ID NO:6:

(i) SEQUENCE CHARACTERISTICS:
         (A) LENGTH: 26 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (ix) FEATURE:
         (A) NAME/KEY: modified_base
         (B) LOCATION: 5
         (D) OTHER INFORMATION: /note="N represents a propane-diol
               substituted residue, as described in Formula I of
               the patent application."

(ix) FEATURE:
         (A) NAME/KEY: misc_feature
         (B) LOCATION: 1..26
         (D) OTHER INFORMATION: /standard_name="PCR PRIMER MD056"

(xi) SEQUENCE DESCRIPTION: SEQ ID NO:6:

AATTNCTTAC TGAAGAAACC AGCAGG                                                              26

(2) INFORMATION FOR SEQ ID NO:7:

(i) SEQUENCE CHARACTERISTICS:
         (A) LENGTH: 35 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (ix) FEATURE:
         (A) NAME/KEY: modified_base
         (B) LOCATION: 5
         (D) OTHER INFORMATION: /note="N represents a propane-diol
               substituted residue, as described in Formula I of
               the patent application."

(ix) FEATURE:
         (A) NAME/KEY: misc_feature
         (B) LOCATION: 1..35
         (D) OTHER INFORMATION: /standard_name="PCR PRIMER MD081"

(xi) SEQUENCE DESCRIPTION: SEQ ID NO:7:

AATTNCGAGC TCGGTACCCG GGGATCCTCT AGAGT                                                    35

(2) INFORMATION FOR SEQ ID NO:8:

(i) SEQUENCE CHARACTERISTICS:
(A) LENGTH: 35 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (ix) FEATURE:
(A) NAME/KEY: modified_base
(B) LOCATION: 5
(D) OTHER INFORMATION: /note="N represents a propane-diol substituted residue, as described in Formula I of the patent application."

(ix) FEATURE:
(A) NAME/KEY: misc_feature
(B) LOCATION: 1..35
(D) OTHER INFORMATION: /standard_name="PCR PRIMER MD080"

(xi) SEQUENCE DESCRIPTION: SEQ ID NO:8:

AGCTNTGCAT GCCTGCAGGT CGACTCTAGA GGATC  35